United States Patent [19]

Colman et al.

[11] Patent Number: 5,097,122
[45] Date of Patent: Mar. 17, 1992

[54] MEDICATION INFUSION SYSTEM HAVING OPTICAL MOTION SENSOR TO DETECT DRIVE MECHANISM MALFUNCTION

[75] Inventors: Fredric C. Colman, Granada Hills; Richard E. Purvis, Glendale, both of Calif.

[73] Assignee: Pacesetter Infusion, Ltd., Sylmar, Calif.

[21] Appl. No.: 509,936

[22] Filed: Apr. 16, 1990

[51] Int. Cl.⁵ .............................................. G01D 5/34
[52] U.S. Cl. .................................. 250/231.14; 604/151
[58] Field of Search ....................... 250/231.14, 231.16, 250/237 G; 604/151, 154

[56] References Cited

U.S. PATENT DOCUMENTS

| | | | |
|---|---|---|---|
| 4,641,027 | 2/1987 | Renner et al. | 250/231.14 |
| 4,667,098 | 5/1987 | Everett | 250/237 G |
| 4,725,723 | 2/1988 | Shimojima | 250/231.14 |

Primary Examiner—David C. Nelms
Assistant Examiner—S. Allen
Attorney, Agent, or Firm—Leslie S. Miller; Stuart O. Lowry

[57] ABSTRACT

An optical motion sensor is provided for monitoring movement of a mechanical device, particularly such as an infusion pump of the type used for controlled delivery of medication to a patient. The motion sensor includes a disk member mounted upon a selected mechanical output component driven by the infusion pump, such that the disk member undergoes displacement during normal pump operation. The disk member defines a pattern of reflective and substantially nonreflective surface zones which are alternately illuminated by a light source during normal pump operation. A light detector responds to the level of reflection from the disk member to provide an output signal which varies according to disk member displacement. This output signal is connected to a controller for comparison with drive signals supplied to the infusion pump, to verify proper mechanical output operation of the pump.

27 Claims, 2 Drawing Sheets

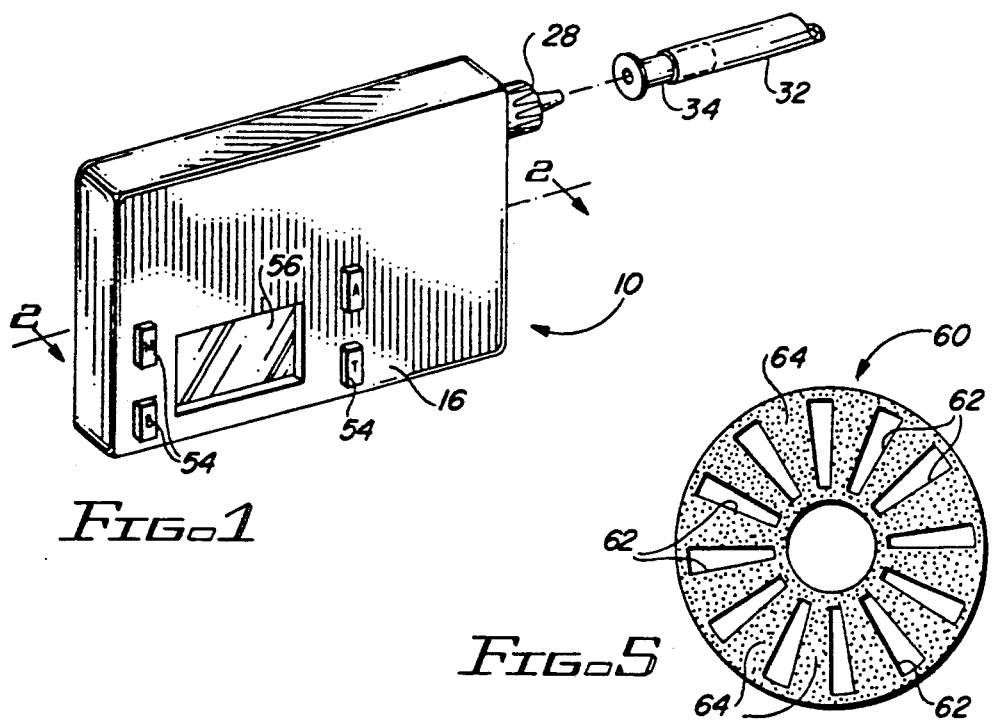
FIG. 1
FIG. 3
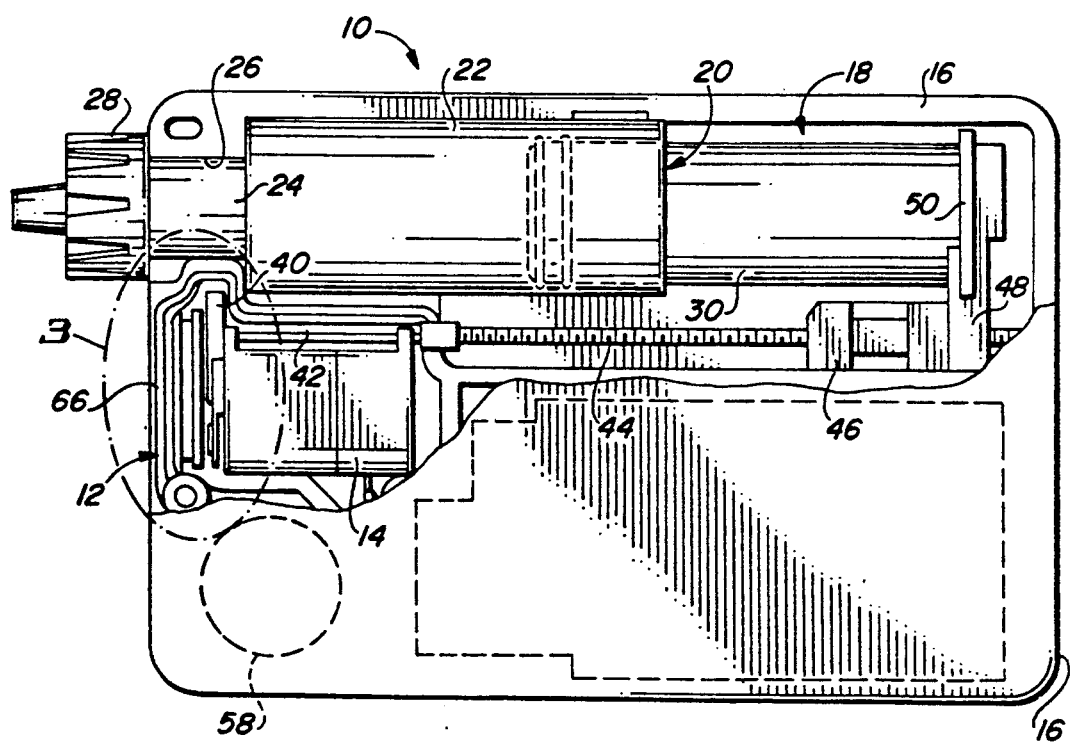
FIG. 2

MEDICATION INFUSION SYSTEM HAVING OPTICAL MOTION SENSOR TO DETECT DRIVE MECHANISM MALFUNCTION

BACKGROUND OF THE INVENTION

Field of the Invention

This invention relates generally to devices and systems for detecting and/or verifying mechanical movements, such as verification of displacement of an output component in a mechanical device. More specifically, this invention relates to an optical motion sensor device particularly designed to monitor and verify proper operation of an infusion pump of the type used for controlled delivery of medication to a patient.

Infusion pump devices and systems are relatively well-known in the medical arts, for use in delivering or dispensing a prescribed medication such as insulin to a patient. In one form, such devices comprise a relatively compact pump housing adapted to receive a syringe carrying a prescribed medication for administration to a patient through infusion tubing and an associated catheter or the like. The infusion pump includes a small drive motor connected via a lead screw assembly for motor-driven advancement of a syringe piston plunger to administer the medication to the patient. Programmable control means are normally provided for operating the drive motor continuously or at periodic intervals to obtain a closely controlled and accurate delivery of medication over an extended time period. Such infusion pumps are utilized to administer insulin and other medications, with an exemplary pump construction being shown and described in U.S. Pat. No. 4,562,751 to Nason et al., U.S. Pat. No. 4,678,408 to Nason et al, and U.S. Pat. No. 4,685,903 to Cable et al. U.S. Pat. No. 4,562,751, U.S. Pat. No. 4,678,408, and U.S. Pat. No. 4,685,903 are hereby incorporated herein by reference.

Infusion pumps of the general type described above have provided significant advantages and benefits with respect to accurate delivery of medication over an extended time period. The infusion pump is often designed to be extremely compact and may thus be adapted to be carried by the patient, for example, by means of a belt clip or the like. As a result, important medication can be administered with precision and in an automated manner, without significant restriction on the patient's mobility or life-style.

The programmable control means for the infusion pump commonly includes internal error sensors which guard against uncontrolled, runaway delivery of medication in the event of pump failure. Accordingly, the control means is normally designed to prevent delivery of excess medication to the patient. However, infusion pumps have not included means for verifying or confirming actual mechanical displacement of the syringe plunger in response to drive signals sent by the control means to the pump drive motor. As such, prior art infusion pumps have not been able to detect mechanical pump failures which, although rare, result in undesirable nondelivery of the medication to the patient.

There exists, therefore, a significant need for improvements in medication infusion pumps, particularly with respect to providing means for monitoring and verifying actual delivery of medication to the patient in response to operation of the pump drive motor. The present invention fulfills this need and provides further related advantages.

SUMMARY OF THE INVENTION

In accordance with the invention, an optical motion sensor is provided for monitoring movement of a selected mechanical output component in a mechanical device. The motion sensor is particularly designed for monitoring and verifying proper operation of an infusion pump of the type used for controlled delivery of medication to a patient. The motion sensor includes optical means for detecting movement of the output component and for generating a corresponding output signal for comparison with pump drive signals to confirm proper pump operation.

The optical motion sensor is particularly designed for integration into an infusion pump having a programmable controller for supplying drive signals on a selected intermittent or continuous basis to a pump drive motor. The drive motor includes a mechanical output connected through a lead screw assembly to the piston plunger of a syringe containing a selected medication for administration to a patient. The syringe is adapted to seat within an appropriate chamber formed in a pump housing, with controlled advancement of the syringe plunger delivering the medication to the patient through a catheter or the like.

The optical motion sensor includes a disk member mounted upon a selected mechanical output component of the infusion pump, such as a rotatable ratchet wheel driven by the drive motor as described in U.S. Pat. No. 4,562,751, U.S. Pat. No. 4,678,408 and U.S. Pat. No. 4,685,903, which are incorporated by reference herein. The disk member defines a pattern of reflective and substantially nonreflective surface zones which are displaced mechanically during proper pump motor operation. This pattern of reflective and nonreflective surface zones are alternately illuminated by a light source, and a light detector responds to the level of reflection from the disk member to provide a varying output signal representing actual disk member displacement.

The output signal is connected to the controller and compared therein with drive signals supplied to the pump motor, for purposes of verifying actual mechanical pump output displacement. In the event that the controller identifies a mismatch between the output signals from the light detector in relation to pump motor drive signals, an appropriate audio and/or visual alarm can be activated to indicate mechanical pump failure.

Other features and advantages of the present invention will become more apparent from the following detailed description, taken in conjunction with the accompanying drawings which illustrate, by way of example, the principles of the invention.

DESCRIPTION OF THE DRAWINGS

These and other advantages of the present invention are best understood with reference to the drawings, in which:

FIG. 1 is a front perspective view illustrating a medication infusion pump adapted for controlled delivery of medication to a patient, and further adapted for use with the optical motion sensor embodying the novel features of the invention;

FIG. 2 is an enlarged rear elevation view of the infusion pump of FIG. 1, with portions broken away to illustrate pump operating components;

FIG. 5 is an enlarged elevational view depicting a reflective disk member forming a portion of the motion sensor;

DETAILED DESCRIPTION OF THE PREFERRED EMBODIMENT

Figure 3:
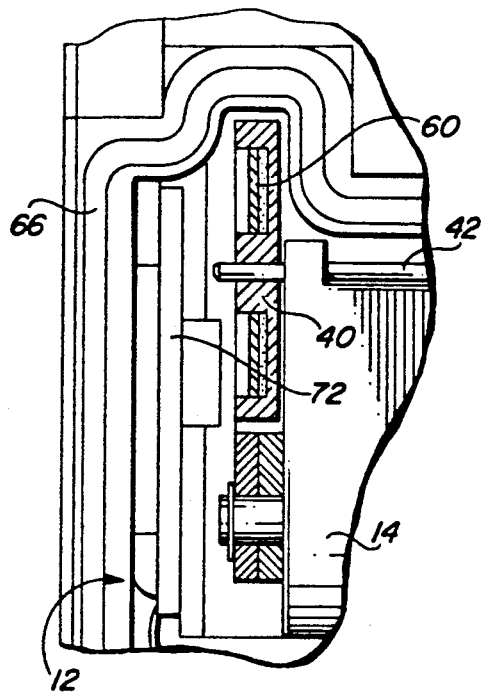
FIG. 3 is a further enlarged fragmented rear elevational view corresponding generally with the encircled region 3 of FIG. 2, and illustrating the optical motion sensor of the present invention.

As shown in the exemplary drawings, an infusion pump referred to generally in FIG. 1 by reference numeral 10 is provided for controlled administration of medication to a patient. In accordance with the invention, the infusion pump 10 includes an optical motion sensor 12 (FIG. 2) for monitoring and verifying proper mechanical output operation of a pump drive motor 14.

The infusion pump 10 has an overall construction and operation which is generally known in the art. More specifically, with reference to FIGS. and 2, the infusion pump 10 includes a relatively compact pump housing 16 defining an elongated chamber 18 (FIG. 2) adapted to receive and support a syringe 20 charged with a selected medication, such as insulin, to be administered to a patient. The medication-containing syringe includes a syringe barrel 22 joined at the front to a luer neck 24 of reduced diametric size to seat snugly within an outlet port 26 formed in the pump housing 16. A female luer fitting 28 is carried on a forward end of the neck 24 and cooperates with the barrel 22 to fix the syringe in a seated position within the housing chamber 18. A syringe piston or plunger 30 extends from the aft end of the barrel 22 and may be advanced into the barrel to deliver the medication therefrom. In this regard, the medication is normally dispensed to the patient through a catheter tube 32 (FIG. 1) or the like having an appropriate male luer fitting 34 engageable with the female luer fitting 28.

The drive motor 14 of the infusion pump 10 is mechanically connected to the syringe plunger 30 for purposes of advancing the plunger in a precision controlled manner to dispense the medication. The illustrative drive motor 14 corresponds with the infusion pump depicted in U.S. Pat. No. 4,562,751, U.S. Pat. No. 4,678,408, and U.S. Pat. No. 4,685,903, which are incorporated by reference herein, although it will be understood that alternative drive motor mechanisms may be used, if desired.

Figure 4:
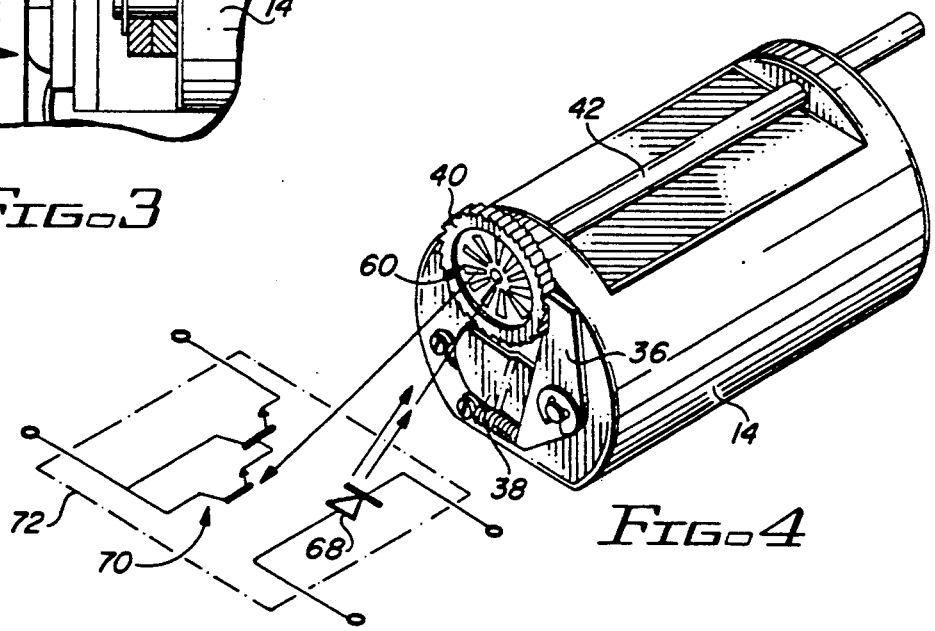
FIG. 4 is an enlarged perspective view depicting a drive motor for the infusion pump, in combination with the optical motion sensor shown partially in schematic form.

More specifically, the illustrative drive motor 14 operates a pair of spring loaded pawls 36 and 38 to obtain incremental rotational advancement of a ratchet wheel 40, as shown best in FIG. 4. The ratchet wheel is mounted at one end of a output shaft 42 which is connected inline with a lead screw 44. As viewed in FIG. 2, the lead screw 44 carries a lead screw nut 46 having a fixture 48 thereon for engaging an enlarged flange 50 on the outboard end of the piston plunger 30. Accordingly, operation of the drive motor 14 rotates the ratchet wheel 40 and lead screw 44 in incremental steps, resulting in advancement of the lead screw nut 46 and piston plunger 30 in a precision controlled manner.

Figure 6:
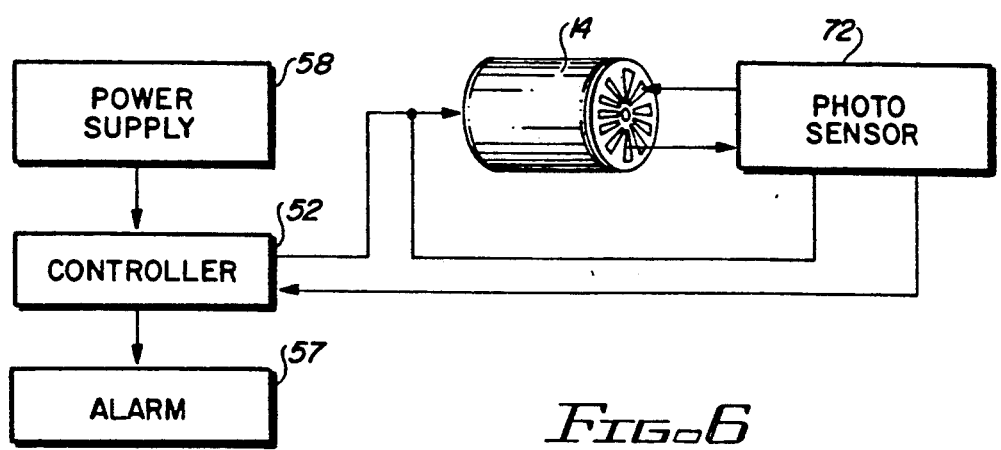
FIG. 6 is a schematic diagram depicting operation of the motion sensor in conjunction with the infusion pump to monitor and verify proper pump output displacement.

As shown in FIGS. 1, 2 and 6, the infusion pump 10 includes a programmable controller 52 for regulating operation of the drive motor 14. As known in the art, the programmable controller 52 can be set by the attending physician, appropriate medical personnel, or the user by use of an array of buttons 54 (FIG. 1) on the front of the pump housing 16, with a corresponding display panel 56 providing appropriate information regarding set status and/or pump operation. The controller 52 is adapted to couple a battery power supply 58 or the like to the drive motor to obtain a desired drive motor operation on a continuous or intermittent basis, in accordance with the controller program.

The optical motion sensor 12 of the present invention is integrated into the pump housing 16 in association with a selected mechanical output component of the drive motor 14. The motion sensor 12 includes small optoelectronic components designed to sense displacement of the associated output component, and thereby detect actual mechanical output movement which correlates with actual delivery of medication to a patient.

In general terms, the motion sensor 12 provides an output signal which varies in a regular manner according to actual mechanical output displacement, and this output signal is connected back to the controller 52 for comparison with drive signals inputted to the drive motor 14. The controller 52 can thus confirm or verify proper mechanical output operation of the infusion pump against actual input drive signals. In the event that this comparison indicates a mechanical output failure, the controller 52 provides an appropriate alarm 57 (FIG. 6), such as activation of an alarm signal on the display panel, and/or an audio alarm, etc.

In the preferred form of the invention as shown in the illustrative drawings, the motion sensor 12 comprises a thin and lightweight disk member 60 mounted on the ratchet wheel 40. The disk member 60 defines an array or pattern of radially projecting reflective surface zones 62 separated by radially projecting substantially nonreflective surface zones 64 (FIGS. 4 and 5). This pattern of reflective and nonreflective zones 62 and 64 is presented in an outboard direction toward an adjacent end wall 66 of the pump housing 16 (FIGS. 2 and 3).

In a preferred form, the disk member 60 comprises an adhesive-backed label having a reflective metallized film which is partially masked by an overlay of flat black ink or paint defining the nonreflective zones 64. FIG. 5 illustrates a combination of twelve reflective zones 62 in alternating array with 12 nonreflective zones 64, although it will be understood that other zone numbers and/or patterns may be used as desired.

The disk member 60 is positioned for illumination by a miniature light source 68, such as a light emitting diode (LED). The light source 68 is focused at a predetermined point to alternately illuminate the reflective and nonreflective zones 62 and 64 on the disk member in accordance with disk member rotation with the ratchet wheel 40. The illumination of the disk member correspondingly results in reflection of light at different levels, wherein the reflected light is detected by a small photodetector 70 which generates an output signal according to the level of reflection. The output signal is connected, as viewed in FIG. 6, to the controller 52. In one preferred form, the light source 68 and photodetector 70 are provided as a photoreflective sensor 72 of the type marketed by Sharp Electronics Corporation of Japan under Model Designation GP2L06.

As shown in FIG. 6, the photoreflective sensor 72 is connected to the power supply 58 simultaneously with connection of an input drive signal to the drive motor 14. Accordingly, during intermittent drive motor energization, the photoreflective sensor 72 is also activated on an intermittent basis to achieve relatively low power consumption. The sensor provides the output signal to the controller 52 which includes internal memory means for comparing the output signal with drive motor input signals. In the event that a mismatch is present between the compared signal information, the appropriate alarm 57 or the like may be activated to identify mechanical pump failure.

In the illustrative form of the invention, the ratchet wheel 40 is designed for incremental rotation to achieve corresponding incremental advancement of the piston plunger 30 and accompanying incremental medication dispensing to the patient. The number of ratchet teeth on the wheel 40 can be correlated with the combined number of reflective and nonreflective surface zones 62 and 64, such that one of the zones will be rotated past, the illuminating sight line of the light source 68 within a prescribed number or rotational increments of the ratchet wheel. For example, in a ratchet wheel having a total of seventy-two ratchet teeth, a disk member 60 having twenty-four total reflective and nonreflective zones will rotate each zone past the light source 68 in three incremental advancements of the ratchet wheel. The controller 52 can be programmed to require detection of a changed level in the output signal from the photoreflective sensor 72 for each three or four advancements of the ratchet wheel. Alternately, other correlated numbers of ratchet wheel teeth and disk member surface zones can be used, as desired.

Figure 7:
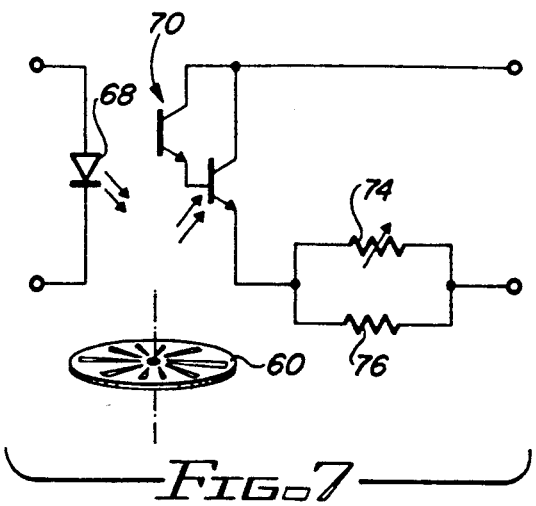
FIG. 7 is a schematic diagram illustrating one alternative preferred form of the optical motion sensor.

In one alternative form of the invention as depicted in FIG. 7, the photoreflective sensor 72 may include a thermistor 74 for automatic compensation in response to temperature variations encountered by the sensor. More specifically, the photoreflective sensor 72 is known to provide a varying output as a function of varying ambient temperature. By connecting a thermistor 74 in parallel with a resistor 76 on one output leg of the sensor 72, automatic compensation for temperature variations may be built into the system.

The optical motion sensor 12 of the present invention thus provides a nonmechanical apparatus for monitoring and verifying displacement of an output component in a mechanical device, such as an infusion pump used to deliver medications to a patient.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A medication infusion system including an arrangement for monitoring the operation of said medication infusion system to ensure that said medication infusion system is operating properly to cause medication to be dispensed to a patient, said system comprising:

a housing including means for mounting a syringe having a plunger therein;

a lead screw mounted for rotation in said housing;

a drive wheel for driving said lead screw;

means for driving said drive wheel to rotate said lead screw;

means mounted on said lead screw for pushing said plunger into said syringe to dispense medication when said lead screw rotates;

a reflective member having a pattern of reflective and substantially nonreflective surface zones thereon, said reflective member being mounted on said drive wheel to displace said reflective and nonreflective surface zones in sequence past a predetermined point; and photoreflective sensor means for illuminating said predetermined point, and for detecting the level of reflection from said reflective member at said predetermined point to monitor movement of said reflective member with said drive wheel.

2. A medication infusion system as defined in claim 1, wherein said photoreflective sensor includes a light source for illuminating said predetermined point, and a photodetector for monitoring the level of reflection from said reflective member and for generating an output signal representative of said level of reflection.

3. A medication infusion system as defined in claim 1, wherein said reflective member comprises a disk member mounted for rotation with said drive wheel, said pattern of reflective and substantially nonreflective surface zones being formed in a generally radial alternating array on one side of said disk member.

4. A medication infusion system as defined in claim 1, wherein said photoreflective sensor generates an output signal representative of said level of reflection, and further including alarm means responsive to said output signal to indicate insufficient movement of said drive wheel.

5. A medication infusion system as defined in claim 1, wherein said driving means comprises a drive motor, and wherein said photoreflective sensor generates an output signal representative of said level of reflection, and further including controller means for comparing said output signal with drive signals inputted to said drive motor and for indicating insufficient movement of said drive wheel in response to the drive signals.

6. A system as defined in claim 1, wherein said reflective member comprises an adhesive backed label disk for mounting onto said drive wheel and having said pattern of surface zones on a front side thereof.

7. A medication infusion system as defined in claim 1, wherein said photoreflective sensor means generates an output signal representing said level of reflection, and wherein said driving means comprises a drive motor having drive signals inputted thereto, the medication infusion system additionally comprising:

controller means for comparing said output signal with the drive signals inputted to said drive motor and for responding thereto to indicate the operational state of said drive motor.

8. A system as defined in claim 7, additionally comprising:

means for compensating said output signal as a function of ambient temperature.

9. A system as defined in claim 7, wherein said controller means includes an alarm for indicating insufficient movement of said reflective member and said lead screw in relation to the drive signals inputted to said drive motor.

10. A system for use in a medication infusion system for monitoring and verifying proper operation of the medication infusion system, said medication infusion system being of the type which operates by engaging the plunger of a syringe to dispense medication to a patient, said system comprising:

a drive motor having drive signals inputted thereto;

mechanical drive means, driven by said drive motor, for driving the plunger of the syringe to dispense medication the patient;

a reflective member having a pattern thereon of reflective and substantially nonreflective surface zones, said reflective member being movable with said lead screw to displace said reflective and nonreflective zones sequentially past a predetermined point;

light source means for illuminating said predetermined point;

reflection detector means for detecting the level of light reflected from said reflective member at said predetermined point and for generating an output signal representing said level of reflection; and controller means for comparing said output signal with the drive signals inputted to said drive motor and for responding thereto to indicate the operational state of said drive motor.

11. A system as defined in claim 10, wherein said controller means includes an alarm for indicating insufficient movement of said reflective member and said lead screw in relation to the drive signals inputted to said drive motor.

12. A system as defined in claim 10, wherein said lead screw is driven by a rotatable wheel, and wherein said reflective member comprises an adhesive backed label disk for mounting onto said wheel and having said pattern for surface zones on a front side thereof.

13. A system, as defined in claim 10, wherein said detector means includes means for compensating said output signal as a function of ambient temperature.

14. In an infusion pump having a drive motor, controller means for inputting drive signals to the drive motor, and at least one mechanical output component displaced by the drive motor and adapted to operate a syringe to deliver medication or the like therefrom in a controlled manner, a sensor-operated infusion pump safety monitoring system, comprising:

a reflective member having a pattern thereon of reflective and substantially nonreflecting surface zones, said reflective member being movable with the mechanical output component to displace said reflective and nonreflective zones sequentially past a predetermined point;

light source means for illuminating said predetermined point; and reflection detector means for detecting the level of light reflected from said reflective member at said predetermined point and for generating an output signal representing said level of reflection;

said controller means including means for comparing said output signal with the drive signals inputted to the drive motor and for responding thereto to indicate the operational state of the drive motor, said controller means providing a fault signal when insufficient movement of said reflective member and the mechanical output component in relation to the drive signals inputted to the drive motor is detected; and means for providing an underinfusion alarm when said controller means provides said fault signal.

15. An optical motion sensor as defined in claim 14, wherein the mechanical output component comprises a rotatable wheel, and wherein said reflective member comprises an adhesive backed label disk for mounting onto said wheel and having said pattern of surface zones on a front side thereof.

16. An optical motion sensor as defined in claim 14, wherein said detector means includes means for compensating said output signal as a function of ambient temperature.

17. An optical motion sensor as defined in claim 14, wherein said mechanical output component comprises a ratchet wheel having a predetermined number of ratchet teeth thereon, said drive motor including means responsive to said drive signals for rotating said ratchet wheel in increments, said reflective member having said pattern of surface zones formed thereon in radial alternating array and with a total number of said surface zones such that the ratio of the number of ratchet teeth and surface zones, one to the other, is a whole number.

18. A medication infusion system including an arrangement for monitoring the operation of said medication infusion system to ensure that said medication infusion system is operating properly to cause medication to be dispensed to a patient, said system comprising:

a housing including means for mounting a syringe having a plunger therein;

a mechanical drive element mounted for driven movement in said housing;

a drive wheel for driving said mechanical drive element;

means for driving said drive wheel to drive said mechanical drive element;

means mounted on said mechanical drive element for pushing said plunger into said syringe to dispense medication when said mechanical drive element is driven into movement;

a reflective member having a pattern of reflective and substantially nonreflective surface zones thereon, said reflective member being mounted on said drive wheel to displace said reflective and nonreflective surface zones in sequence past a predetermined point; and photoreflective sensor for illuminating said predetermined point, and for detecting the level of reflection from said reflective member at said predetermined point to monitor movement of said reflective member with said drive wheel.

19. A medication infusion system as defined in claim 18, wherein said photoreflective sensor includes a light source for illuminating said predetermined point, and a photodetector for monitoring the level of reflection from said reflective member and for generating an output signal representative of said level of reflection.

20. A medication infusion system as defined in claim 18, wherein said reflective member comprises a disk member mounted for rotation with said drive wheel, said pattern of reflective and substantially nonreflective surface zones being formed in a generally radial alternating array on one side of said disk member.

21. A medication infusion system as defined in claim 18, wherein said photoreflective sensor generates an output signal representative of said level of reflection, and further including alarm means responsive to said output signal to indicate insufficient movement of said drive wheel.

22. A medication infusion system as defined in claim 18, wherein said driving means comprises a drive motor, and wherein said photoreflective sensor generates an output signal representative of said level of reflection, and further including controller means for comparing said output signal with drive signals inputted to said drive motor and for indicating insufficient movement of said drive wheel in response to the drive signals.

23. A medication infusion system as defined in claim 18, wherein said mechanical drive element comprises:
   a lead screw mounted for rotation in said housing, said lead screw being driven to rotate by said drive wheel when said drive wheel is driven by said driving means, and said lead screw pushing said plunger into said syringe to dispense medication when said lead screw rotates.

24. A system as defined in claim 18, wherein said reflective member comprises an adhesive backed label disk for mounting onto said drive wheel and having said pattern of surface zones on a front side thereof.

25. A medication infusion system as defined in claim 18, wherein said photoreflective sensor means generates an output signal representing said level of reflection, and wherein said driving means comprises a drive motor having drive signals inputted thereto, the medication infusion system additionally comprising:
   controller means for comparing said output signal with the drive signals inputted to said drive motor and for responding thereto to indicate the operational state of said drive motor.

26. A system as defined in claim 25, additionally comprising:
   means for compensating said output signal as a function of ambient temperature.

27. A system as defined in claim 25, wherein said controller means includes an alarm for indicating insufficient movement of said reflective member and said lead screw in relation to the drive signals inputted to said drive motor.

* * * * *